US005595715A

United States Patent [19]
Roth

[11] Patent Number: 5,595,715
[45] Date of Patent: Jan. 21, 1997

[54] SYNTHESIS OF TETRAMETHYLAMMONIUM ALUMINOSILICATE AND USE THEREOF

[75] Inventor: Wieslaw J. Roth, Sewell, N.J.

[73] Assignee: Mobil Oil Corporation, Fairfax, Va.

[21] Appl. No.: 319,915

[22] Filed: Oct. 7, 1994

[51] Int. Cl.[6] .................................................. C01B 33/26
[52] U.S. Cl. .................. 423/328.1; 423/385; 423/387; 423/705; 423/707
[58] Field of Search ....................... 423/701, 705, 423/707, 718, 328.1, 385, 387

[56] References Cited

U.S. PATENT DOCUMENTS

| | | | |
|---|---|---|---|
| 4,705,674 | 11/1987 | Araya et al. | 423/705 |
| 4,762,010 | 8/1988 | Borghard et al. | 73/865.5 |
| 4,834,961 | 5/1989 | Fajula et al. | 423/701 |
| 5,098,684 | 3/1992 | Kresge et al. | 423/277 |
| 5,102,643 | 4/1992 | Kresge et al. | 423/328 |
| 5,108,725 | 4/1992 | Beck et al. | 423/705 |
| 5,110,572 | 5/1992 | Calabro et al. | 423/705 |
| 5,156,829 | 10/1992 | McCullen et al. | 423/718 |
| 5,211,934 | 5/1993 | Kresge et al. | 423/706 |
| 5,215,737 | 6/1993 | Chu et al. | 423/706 |
| 5,250,282 | 10/1993 | Kresge et al. | 423/705 |
| 5,308,602 | 5/1994 | Calabro et al. | 423/705 |

OTHER PUBLICATIONS

O'Bannon, *Dictionary of Ceramic Science & Engineering* p. 230, 1984.
*High Resolution Solid-State NMR of Silicates and Zeolites*, by G. Engelhardt and D. Michel, (published by John Wiley & Sons, 1987) 96–99 (no month).

Primary Examiner—Mark L. Bell
Assistant Examiner—David Sample
Attorney, Agent, or Firm—Malcolm D. Keen; Peter W. Roberts

[57] ABSTRACT

There is provided a method for the preparation of tetramethylammonium aluminosilicate from tetramethylammonium hydroxide, a solid source of silica and a hydrolyzable aluminum compound. Tetramethylammonium aluminosilicate prepared by the above method is useful for the synthesis of M41S.

10 Claims, No Drawings

SYNTHESIS OF TETRAMETHYLAMMONIUM ALUMINOSILICATE AND USE THEREOF

RELATED APPLICATIONS

The present invention is related by subject matter to U.S. application Ser. No. 08/319,914 (Mobil Docket No. 7469), filed concurrently herewith.

FIELD OF THE INVENTION

The present invention relates to a method for the preparation of tetramethylammonium aluminosilicate. More particularly, the present invention relates to the preparation of tetramethylammonium aluminosilicate solution for the synthesis of M41S.

BACKGROUND OF THE INVENTION

Tetramethylammonium (TMA) aluminosilicate is an important raw material for molecular sieve preparations. The soluble aluminosilicate salts of the quaternary ammonium cations, TMA in particular, are useful reagents for the synthesis of ultra large pore M41S. They are important as alkali sources of aluminosilicate dispersed on a molecular scale.

While the basic chemical principles would suggest that their preparation should be trivial, in practice, the apparently obvious approaches, such as described in the book "High-Resolution Solid-State NMR of Silicates and Zeolites" by G. Engelhardt and D. Michel, (published by John Wiley & Sons, 1987) on pages 96–99, have either failed or turned out to be impractical and/or inconvenient. Synthesis of TMA aluminosilicate, as reported by D. Hoebbel, G. Garzo, K. Ujszaszi G. Engelhardt, B. Fahlke and A. Vargha in Z. Anorg. Allg. Chemie., Vol. 484, pp. 7–21 (1982), involves dissolution of Al in TMA hydroxide, which is cumbersome and lengthy and liberates explosive hydrogen gas. Freshly precipitated Al hydrous oxide can also be used, but it requires multiple washing of the gelatinous precipitate.

Therefore, it is an object of the present invention to provide a convenient synthesis method for the preparation of TMA aluminosilicate. It is a further object of the present invention to provide a TMA aluminosilicate reagent for use in the synthesis of M4!S.

SUMMARY OF THE INVENTION

The present invention therefore includes a method for the synthesis of TMA aluminosilicate which comprises:

admixing a source of solid silica and tetramethylammonium hydroxide and heating the admixture at a temperature in the range of from about 40° C. to about 150° to produce a tetramethylammonium silicate intermediate product; and dissolving a hydrolyzable aluminum compound in said tetramethylammonium silicate intermediate product to produce tetramethylammonium aluminosilicate.

The present invention further includes a method for synthesizing a composition of matter comprising an inorganic, porous, non-layered crystalline phase material exhibiting, after calcination, an X-ray diffraction pattern with at least one peak at a d-spacing greater than about 18 Angstrom Units with a relative intensity of and a benzene adsorption capacity of greater than 15 grams benzene per 100 grams of said material at 50 torr and 25° C., said method comprising the steps of:

(a) preparing a mixture capable of forming said composition, said mixture comprising a source of silica, a source of alumina, an organic (R') agent and a solvent or solvent mixture, wherein R' comprises an ion of the formula $R_1R_2R_3R_4Q^+$, wherein Q is nitrogen or phosphorus and wherein at least one of $R_1$, $R_2$, $R_3$ and $R_4$ is aryl or alkyl of from 6 to about 36 carbon atoms or combinations thereof, the remainder of $R_1$, $R_2$, $R_3$ and $R_4$ being selected from the group consisting of hydrogen, alkyl of from 1 to 5 carbon atoms and combinations thereof;

(b) maintaining said mixture under sufficient conditions of pH, temperature and time for formation of said composition of matter; and (c) recovering said composition of matter, wherein said mixture of step (a) comprises tetramethylammonium aluminosilicate as said source of silica and said source of alumina.

DETAILED DESCRIPTION OF THE INVENTION

The present invention relates to the synthesis of TMA aluminosilicate from TMA hydroxide and a solid source of silica. The synthesis involves mixing the TMA hydroxide and silica reagents and heating of the reagents. The method of the present invention may also be carried out in situ, as part of preforming the reaction mixture in molecular sieve preparations.

Suitable sources of silica for the present invention include amorphous silicas. The silica is added in an amount in the range of from about 1 wt. % to about 30 wt. %.

The TMA hydroxide is added in an amount in the range of from about 1 wt. % to about 25 wt. %. The remainder of the reaction mixture is not significant.

The TMA hydroxide and silica are mixed and maintained at a temperature in the range of from about 40° C. to about 150° C. at autogenous pressure. Generally the heating is carried out for a time in the range of from about 1 minute to about 24 hours and preferably for about 1 hour to produce a TMA silicate intermediate product.

TMA silicate intermediate product having a TMA/Si ratio in the range of from about 0.1 to about 2 is produced by the method of the present invention.

TMA aluminosilicate is prepared by dissolving aluminum isopropoxide or other hydrolyzable or basic aluminum compounds, such as sodium aluminate, in the TMA silicate as prepared above. Aluminum isopropoxide is preferred.

The hydrolyzable aluminum compound is added in an amount corresponding to a silica to alumina ratio in the range of from about 2 to about infinity.

The TMA silicate and aluminum isopropoxide are mixed and heated at a temperature in the range of from about 25° C. to about 150° C., and preferably in the range of from about 40° C. to about 150° C., at autogenous pressure. Generally the heating is carried out for a time in the range of from about 1 minute to about 24 hours.

The TMA hydroxide, solid source of silica and aluminum isopropoxide may also be mixed without first forming TMA silicate intermediate product. Further, TMA silicate from any source may be mixed with aluminum isopropoxide to form TMA aluminosilicate of the present invention.

TMA aluminosilicate product having a silica/alumina ratio in the range of from about 2 to infinity is produced by the method of the present invention.

The method of the present invention may be useful for the synthesis of other soluble aluminosilicate salts of the quaternary ammonium ions, such as tetraethylammonium, tetrapropylammonium tetrabutylammonium, trimethylbenzyl, as well as other elements that can form soluble salts with these cations and are available as alkoxides or other soluble or hydrolyzable coordination compounds.

TMA aluminosilicate may be used in the preparation of a synthetic composition of matter comprising an ultra-large pore size crystalline phase. This material may be an inorganic, porous, non-layered, crystalline phase material which can be characterized (in its calcined form) by an X-ray diffraction pattern with at least one peak at a d-spacing greater than about 18 Angstroms with a relative intensity of 100 and a benzene sorption capacity of greater than 15 grams of benzene per 100 grams of the material at 50 torr and 25° C. This material, identified as M41S, and its preparation and properties are described in further detail in U.S. Pat. No. 5,102,643, incorporated herein by reference. TMA aluminosilicate prepared by the method of the present invention may be formed in situ without explicit preparation in M41S synthesis.

The preferred form of the crystalline material is an inorganic, porous material having a hexagonal arrangement of uniformly sized pores with a maximum perpendicular cross-section pore diameter of at least about 13 Å Units, and typically within the range of from about 13 Å Units to about 200 Å Units, identified as MCM-41. This material exhibits a hexagonal electron diffraction pattern that can be indexed with a $d_{100}$ value greater than about 18 Angstroms which corresponds to at least one peak in the X-ray diffraction pattern. This material and its preparation and properties are described in further detail in U.S. Pat. No. 5,098,684, incorporated herein by reference. TMA aluminosilicate prepared in accordance with the present invention is particularly useful for the preparation of high alumina content MCM-41, e.g. with a silica to alumina ratio less than about 30:1, more particularly less than about 20:1.

The methodology and procedures herein describe the synthesis of the crystalline oxide materials which are formed by the use of the broad range of amphiphilic compounds with particular emphasis on cationic amphiphiles. These compounds serve as liquid crystal templates in directing the formation of these new species. In a general context the invention involves the formation of highly-ordered inorganic oxide structures in any medium wherein the inorganic oxide structure that forms is defined by the solvent domains (e.g., aqueous domains) in the liquid crystalline structures. Optionally, the organic amphiphile may be removed by washing and drying, or by calcination in air, which then leaves a porous inorganic material with highly uniform, accessible pores.

The pore diameters of mesoporous, inorganic phases of this invention may also be altered by the addition of auxiliary organics to the reaction mixture. A variety of organic molecules of varying polarity may serve as auxiliary organic swelling agents in the preparation of the mesoporous materials. A variety of nonpolar organics, such as alkylated aromatics and straight or branched chain hydrocarbons are effective in increasing the pore dimension of these materials. Agents which produce swelled versions of the hexagonal phase as determined from X-ray powder diffraction patterns (3–4 peaks related by hexagonal constraints) are generally nonpolar aromatics possessing short aliphatic chains. Straight and branched chain hydrocarbons in the $C_5$–$C_{12}$ range are also effective in increasing pore size; however, the products often exhibit an apparent mixture of phases. Polar organic species, including alcohols, aldehydes, ketones and ethers, were found to be ineffective in increasing pore size of these materials, and in several cases, were found to disrupt the synthesis resulting in the isolation of completely amorphous materials. These results support a swelling mechanism in which the auxiliary organic is solubilized by surfactant micelles. Organics which are non-polar and thus hydrophobic are susceptible to solubilization in the micellar interior and are found to be effective swelling agents. Those organics which have considerable polar character are insoluble in the micelles interior and are therefore incapable of micellar swelling. These species produce no increase in pore dimension of the resulting products. These results are consistent with established principles concerning the concept of organic solubilization in micellar systems.

Although the reaction mixtures of the present invention contain several other chemical components/phases/ions which will affect the CMC, the overall surfactant concentrations (surfactant:total water) are always well above the CMC. Thus, in the present invention, a variety of amphiphile types have been employed as liquid crystal templates in the formation of novel mesoporous materials. Furthermore, alteration of even one type of amphiphile may lead to the formation of varied pore dimension.

In the preparation of mesoporus phases described herein, the amphiphile chain length is reflected in the nature of the final product. The effect of chain length variation of alkyltrimethylammonium amphiphile cations used in the synthesis of the present mesoporous materials is clearly demonstrated by the variation in pore diameter of the final products. A range of pore sizes for the hexagonal materials is possible based on the carbon chain length. For example, the hexagonal phase of the mesoporous material may be prepared with alkyltrimethylammonium surfactant cations of carbon chain length $C_9$–$C_{16}$, and these materials will exhibit pore sizes increasing with increasing carbon chain length.

The exploitation of the properties of amphiphilic compounds and their aggregated micellar forms in the formation of a variety of new inorganic oxide phases is described of herein. In addition, a more general concept involves the formation of inorganic oxide structures formed from any aqueous or non-aqueous liquid crystal-containing medium. Another example of a novel liquid crystal synthesis system is the formation of inorganic oxide structures from reverse micelle systems. In these systems, at high amphiphile concentration, the liquid crystal template might be the water phase with the inorganic structure forming in the "oil" phase.

The oxide materials described herein may be inorganic, porous materials having a pore size of at least about 13 Angstroms. More particularly, the pore size of the present materials may be within the range of from about 13 Angstroms to about 200 Angstroms. Certain of these novel oxide compositions may exhibit a hexagonal electron diffraction pattern that can be indexed with a $d_{100}$ value greater than about 18 Angstroms, and a benzene adsorption capacity of greater than about 15 grams benzene/100 grams crystal at 50 torr and 25° C. Certain of these oxide materials may have a hexagonal arrangement of uniformly sized pores.

To the extent desired, the original ions of the as-synthesized material described herein can be replaced in accordance with techniques well known in the art, at least in part, by ion exchange with other ions. Examples of such replacing ions include metal ions, hydrogen ions, hydrogen precursor, e.g. ammonium, ions and mixtures thereof. Particular examples of such ions are those which tailor the catalytic activity for certain hydrocarbon conversion reactions. Replacing ions include hydrogen, rare earth metals and metals of Groups IA (e.g. K), IIA (e.g. Ca), VIIA (e.g. Mn), VIIIA (e.g. Ni), IB (e.g. Cu), IIB (e.g. Zn), IIIB (e.g. In), IVB (e.g. Sn), and VIIB (e.g. F) of the Periodic Table of the Elements (Sargent-Welch Scientific Co. Cat. No. S-18806, 1979) and mixtures thereof.

Certain of the oxide materials described herein may be readily identified as crystalline materials. The term "crystalline" is meant herein as having sufficient order to produce at least one peak in a diffraction pattern from electromagnetic radiation or particle beams. These crystalline materials may have a diffraction pattern produced, for example, by X-ray, electron or neutron diffraction. These crystalline materials may have sufficient thermal stability to retain the crystallinity thereof after being subjected to calcination conditions to remove organic material from the as-synthesized forms thereof.

Certain of the oxide materials described herein may be readily identified as mesoporous materials. These mesoporous materials may have extremely large pore windows, and high sorption capacity. The term "mesoporous" is used here to indicate materials having pores within the range of from about 13 Angstroms to about 200 Angstroms. The materials described herein may have uniform pores within the range of from about 13 Angstroms to about 200 Angstroms, more usually from about 15 Angstroms to about 100 Angstroms. For the purposes of this disclosure, a working definition of "porous" is a material that adsorbs at least 1 gram of a small molecule, such as Ar, $N_2$, n-hexane or cyclohexane, per 100 grams of the solid.

Certain of the porous oxide materials described herein can be distinguished from other porous inorganic solids by the regularity of their large open pores, whose pore size is greater than that of microporus zeolites, but whose regular arrangement and uniformity of size (pore size distribution within a single phase of, for example, ±25%, usually ±15% or less of the average pore size of that phase) resemble those of zeolites.

Certain forms of the present materials may give rise to characteristic X-ray diffraction patterns, which serve to identify these materials as hexagonal or cubic, as well as to distinguish these materials from lamellar materials or other materials such as known microporus zeolites, layered materials, pillared materials and amorphous materials. Such patterns may have at least two peaks. The positions of these peaks vary with changes in the pore diameters of the materials, but the ratios of d-spacings of those peaks will remain fixed. Using $d_1$ to indicate the d-spacing of the strongest peak in the X-ray diffraction pattern (relative intensity=100), the X-ray diffraction pattern of certain materials produced using amphiphilic compounds exhibit $d_1$ at a position greater than about 18 Angstroms d-spacing and at least one additional weaker peak with d-spacing $d_2$ such that the ratios of these d-spacings relative to $d_1$ correspond to the ranges given in X-ray diffraction pattern Tables set forth hereinafter.

The hexagonal form of the present material, MCM-41 may have an X-ray diffraction pattern with one or more peaks. If only one peak is observed in this pattern, it may be necessary to employ more sensitive techniques, such as electron diffraction by TEM as described hereinafter, in order to confirm the hexagonal symmetry of MCM-41.

X-ray patterns of MCM-41 having 2 or more peaks may have the values given in Table 1.

TABLE 1

| d-spacing Angstroms | $d_n/d_1$ | Relative Intensity |
|---|---|---|
| $d_1 \geq \sim 18$ | 1.0 | 100 |
| $d_2$ | 0.58 ± 0.06 | W |

X-ray patterns of MCM-41 having 3 or more peaks may have the values given in Table 2.

TABLE 2

| d-spacing Angstroms | $d_n/d_1$ | Relative Intensity |
|---|---|---|
| $d_1 \geq \sim 18$ | 1.0 | 100 |
| $d_2$ | 0.58 ± 0.06 | W |
| $d_3$ | 0.50 ± 0.02 | W |

X-ray patterns of MCM-41 having 4 or more peaks may have the values given in Table 3.

TABLE 3

| d-spacing Angstroms | $d_n/d_1$ | Relative Intensity |
|---|---|---|
| $d_1 \geq \sim 18$ | 1.0 | 100 |
| $d_2$ | 0.58 ± 0.06 | W |
| $d_3$ | 0.50 ± 0.02 | W |
| $d_4$ | 0.38 ± 0.02 | W |

The most regular preparations of the hexagonal form of the present mesoporous material give an X-ray diffraction pattern with a few distinct maxima in the extreme low angle region. The positions of these peaks approximately fit the positions of the hk0 reflections from a hexagonal lattice. The X-ray diffraction pattern, however, is not always a sufficient indicator of the presence of these materials, as the degree of regularity in the microstructure and the extent of repetition of the structure within individual particles affect the number of peaks that will be observed. Indeed, preparations with only one distinct peak in the low angle region of the X-ray diffraction pattern have been found to contain substantial amounts of the present material in them. Other techniques to illustrate the microstructure of this material are transmission electron microscopy and electron diffraction. Properly oriented specimens of the hexagonal form of the present material show a hexagonal arrangement of large channels and the corresponding electron diffraction pattern gives an approximately hexagonal arrangement of diffraction maxima. The $d_{100}$ spacing of the electron diffraction patterns is the distance between adjacent spots on the hk0 projection of the hexagonal lattice and is related to the repeat distance $a_0$ between channels observed in the electron micrographs through the formula $d_{100}=a_0\sqrt{3}/2$. This $d_{100}$ spacing observed in the electron diffraction patterns corresponds to the d-spacing of a low angle peak in the X-ray diffraction pattern of the material. The most highly ordered preparations of MCM-41 obtained so far have 20–40 distinct spots observable in the electron diffraction patterns. These patterns can be indexed with the hexagonal hk0 subset of unique reflections of 100, 110, 200, 210, etc., and their symmetry-related reflections.

In its calcined form, the crystalline mesoporous material described herein may have an X-ray diffraction pattern with at least one peak at a position greater than about 18 Angstrom Units d-spacing (4,909 degrees two-theta for Cu K-alpha radiation) which corresponds to the $d_{100}$ value of the electron diffraction pattern of the material, and an equilibrium benzene adsorption capacity of greater than about 15 grams benzene/100 grams crystal at 50 torr and 25° C. (basis: crystal material having been treated in an attempt to insure no pore blockage by incidental contaminants, if necessary).

Certain of the calcined crystalline non-layered materials described herein may be characterized by an X-ray diffraction pattern with at least two peaks at positions greater than about 10 Angstrom Units d-spacing (8,842 degrees two-theta for Cu K-alpha radiation), at least one of which is at a position greater than about 18 Angstrom Units d-spacing, and no peaks at positions less than about 10 Angstrom units d-spacing with relative intensity greater than about 20% of the strongest peak. The X-ray diffraction pattern of calcined materials described herein may have no peaks at positions less than about 10 Angstrom units d-spacing with relative intensity greater than about 10% of the strongest peak. In any event, at least one peak in the X-ray diffraction pattern will have a d-spacing that corresponds to the $d_{100}$ value of the electron diffraction pattern of the material.

Certain forms of this material appear to have a hexagonal arrangement of large open channels that can be synthesized with open internal diameters from about 13 Angstroms to about 200 Angstroms. These forms are referred to herein as hexagonal forms. The term "hexagonal" is intended to encompass not only materials that exhibit mathematically perfect hexagonal symmetry within the limits of experimental measurement, but also those with significant observable deviations from that ideal state. A working definition as applied to the microstructure of the hexagonal form of the present mesoporous material would be that most channels in the material would be surrounded by six nearest neighbor channels at roughly the same distance. Defects and imperfections may cause significant numbers of channels to violate this criterion to varying degrees, depending on the quality of the material's preparation. Samples which exhibit as much as ±25% random deviation from the average repeat distance between adjacent channels still clearly give recognizable images of the hexagonal form of the present ultra-large pore materials. Comparable variations are also observed in the $d_{100}$ values from the electron diffraction patterns.

To illustrate the nature of the mesoporous material described herein, samples of these materials may be studied by transmission electron microscopy (TEM). TEM is a technique used to reveal the microscopic structure of materials, including crystalline materials.

In order to illuminate the microstructure of materials by TEM, samples must be thin enough for an electron beam to pass through them, generally about 500–1000 Angstrom units or so thick. When the crystals of the present materials are too thick, they should be prepared for study by ultramicrotomy. While time consuming, this technique of sample preparation is quite familiar to those skilled in the art of electron microscopy. The materials may be embedded in a resin, e.g., a commercially available low viscosity acrylic resin L.R. WHITE (hard), which is then cured at about 80° C. for about 1½ hours. Thin sections of the block may be cut on an ultramicrotome using a diamond knife and sections in the thickness range 500–1000 Angstrom units may be collected on fine mesh electron microscope support grids. An LKB model microtome with a 45° C. diamond knife edge may be used; the support grids may be 400 mesh copper grids. After evaporation of a thin carbon coating on the sample to prevent charging in the microscope (light gray color on a white sheet of paper next to the sample in the evaporator), the samples are ready for examination in the TEM.

High resolution TEM micrographs show projections of structure along the direction that the sample is viewed. For this reason, it is necessary to have a sample in specific orientations to see certain details of the microstructure of the material. For crystalline materials, these orientations are most easily chosen by observing the electron diffraction pattern (EDP) that is produced simultaneously with the electron microscope image. Such EDP's are readily produced on modern TEM instruments using, e.g., the selected area field limiting aperture technique familiar to those skilled in the art of electron microscopy. When an EDP with the desired arrangement of diffraction spots is observed, the corresponding image of the crystal giving that EDP will reveal details of the microstructure along the direction of projection indicated by the EDP. In this way, different projections of a crystal's structure can be observed and identified using TEM.

In order to observe the salient features of the hexagonal form of the present mesoporous material, it is necessary to view the material in an orientation wherein the corresponding EDP gives a hexagonal arrangement of diffraction spots from a single individual crystal. If multiple crystals are present within the field limiting aperture, overlapping diffraction patterns will occur that can be quite difficult to interpret. The number of diffraction spots observed depends to a degree upon the regularity of the crystalline arrangement in the material, among other things. At the very least, however, the inner ring of bright spots should be observed to obtain a good image. Individual crystals can be manipulated by specimen tilt adjustments on the TEM until this orientation is achieved. More often, it is easier to take advantage of the fact that the specimen contains many randomly oriented crystals and to simply search through the sample until a crystal giving the desired EDP (and hence orientation) is located.

Microtomed samples of materials may be examined by the techniques described above in a JEOL 200 CX transmission electron microscope operated at 200,000 volts with an effective 2 Angstrom objective aperture in place. The instrument has a point-to-point resolution of 4.5 Angstroms. Other experimental arrangements familiar to one skilled in the art of high resolution (phase contrast) TEM could be used to produce equivalent images provided care is taken to keep the objective lens on the underfocus (weak lens) side of the minimum contrast lens current setting.

The application of the above-mentioned TEM techniques to particular samples is described in Example 23 of the aforementioned U.S. Pat. No. 5,098,684.

X-ray patterns of the cubic form of the present material (hereinafter also referred to as MCM-48) having 2 or more peaks may have the values given in Table 4.

TABLE 4

| d-spacing Angstroms | $d_n/d_1$ | Relative Intensity |
| --- | --- | --- |
| $d_1 \gtrsim \sim 18$ | 1.0 | 100 |
| $d_2$ | 0.87 ± 0.06 | W–M |

X-ray patterns of MCM-48 having 3 or more peaks may have the values given in Table 5.

TABLE 5

| d-spacing Angstroms | $d_n/d_1$ | Relative Intensity |
| --- | --- | --- |
| $d_1 \geq \sim 18$ | 1.0 | 100 |
| $d_2$ | $0.87 \pm 0.06$ | W–M |
| $d_3$ | $0.52 \pm 0.04$ | W |

X-ray patterns of MCM-48 having 5 or more peaks may have the values given in Table 6.

TABLE 6

| d-spacing Angstroms | $d_n/d_1$ | Relative Intensity |
| --- | --- | --- |
| $d_1 \geq \sim 18$ | 1.0 | 100 |
| $d_2$ | $0.87 \pm 0.06$ | W–M |
| $d_3$ | $0.55 \pm 0.02$ | W |
| $d_4$ | $0.52 \pm 0.01$ | W |
| $d_5$ | $0.50 \pm 0.01$ | W |

If the reaction mixture has a composition outside the scope of the present invention, a lamellar form of an oxide material may be produced. X-ray patterns of this lamellar form of the material having 2 or more peaks may have the values given in Table 7.

TABLE 7

| d-spacing Angstroms | $d_n/d_1$ | Relative Intensity |
| --- | --- | --- |
| $d_1 \geq \sim 18$ | 1.0 | 100 |
| $d_2$ | $0.50 \pm 0.06$ | W |

X-ray patterns of this lamellar material having 3 or more peaks may have the values given in Table 8.

TABLE 8

| d-spacing Angstroms | $d_n/d_1$ | Relative Intensity |
| --- | --- | --- |
| $d_1 \geq \sim 18$ | 1.0 | 100 |
| $d_2$ | $0.50 \pm 0.06$ | W |
| $d_3$ | $0.33 \pm 0.06$ | W |

X-ray patterns of this lamellar material having 4 or more peaks may have the values given in Table 9.

TABLE 9

| d-spacing Angstroms | $d_n/d_1$ | Relative Intensity |
| --- | --- | --- |
| $d_1 \geq \sim 18$ | 1.0 | 100 |
| $d_2$ | $0.50 \pm 0.06$ | W |
| $d_3$ | $0.33 \pm 0.06$ | W |
| $d_4$ | $0.25 \pm 0.06$ | W |

The X-ray diffraction pattern for the lamellar material has no peaks at positions above 10 degrees 2 theta with an intensity above 10% of the strongest peak.

Most forms of MCM-41 and MCM-48 are quite thermally stable. For example, the as-synthesized forms of these materials may be subjected to calcination sufficient to remove organics, e.g., occluded surfactants from the reaction mixtures, without measurably degrading the crystallinity of the materials, as noted by changes in the X-ray diffraction patterns of the calcined materials in comparison with the X-ray diffraction patterns of the as-synthesized materials. It should be noted, however, that the presence or absence of organic material within the channels of the porous material will substantially affect the relative intensities of the peaks listed in the Tables, particularly resulting in enhanced relative intensities of the shorter d-spacing peaks. The ratios of d-spacings $d_n/d_1$, however, will not be substantially affected. These calcination conditions may include calcination of the as-synthesized material in nitrogen at 540° C. for one hour, followed by calcination in air at 540° C. for 6 hours. The above-mentioned X-ray diffraction pattern Tables for MCM-41 and MCM-48 were mostly derived from the calcined forms of these materials, which were calcined under the above-mentioned conditions including a temperature of 540° C. Accordingly, these X-ray diffraction pattern Tables especially pertain to forms of MCM-41 and MCM-48, which are calcined one or more times under these conditions. However, it will be understood that the d-spacing ratios $d_n/d_1$ in these X-ray diffraction pattern Tables also pertain to other forms of MCM-41 and MCM-48, including as-synthesized forms or other forms, such as where occluded surfactant from the reaction mixture has been totally or partially removed by other treatments, such as calcination under different conditions, washing with an appropriate solvent, ion exchange or combinations of such treatments. Material in the channels of these materials may affect the relative intensities of the peaks in the Tables.

Certain as-synthesized forms of MCM-41 and MCM-48 may not be sufficiently thermally stable to withstand calcination conditions without undergoing substantial degradation in crystallinity and/or porosity. However, certain thermally unstable, as-synthesized forms of MCM-41 and MCM-48 may be stabilized by a stabilization treatment disclosed in U.S. Pat. No. 5,156,829, the entire disclosure of which is expressly incorporated herein by reference. This stabilization treatment involves contacting the material with a compound of the formula $$M'X'_2Y'_n$$

where M' is boron, aluminum, silicon or titanium; X' represents alkyl halides having from 1–6 carbon atoms and/or alkoxides having 1–6 carbon atoms; Y' represents X and/or alkyls with 1–12 carbon atoms; and n=1–2. Examples of compounds of the formula $M'X'_2Y'_n$ are tetraethylorthosilicate, tetramethylorthosilicate, titanium tetraethoxide, aluminum tri-sec-butoxide and aluminum tri-iso-butoxide. The treatment mixture containing crystalline material and $M'X'_2Y'_2$ may also include solvents as are known in the art, preferably organic solvents such as alcohols and diols having 1 to 6 carbon atoms ($C_{1-6}$). The ratio of crystalline material to treatment compound may vary within wide limits, e.g., from about 1:100 to about 100:1. The temperature at which the treatment method may be carried out is limited, as a practical matter, only by the freezing or boiling point (including the boiling point under pressure) of the treatment mixture, and the time of contacting is not critical and may be, for example, from about 1 to about 24 hours, preferably from about 1 to about 12 hours. After treatment, the treated product is preferably calcined, preferably in the presence of oxygen, under conditions sufficient to convert the compound to an oxide of M'.

Without being bound by any theory, it is theorized that this stabilization treatment of MCM-41 and MCM-48 results in the insertion of additional matter into the pore walls, thereby resulting in stronger, more stable pore walls. It will be understood that the above-mentioned X-ray diffraction pattern Tables for MCM-41 and MCM-48 represent forms of MCM-41 and MCM-48, which have been subjected to stabilization treatments, such as those disclosed in U.S. Pat. No. 5,156,829.

The calcined inorganic, crystalline material described herein may have a pore size of about 13 Angstroms or greater as measured by physisorption measurements, hereinafter more particularly set forth. It will be understood that pore size refers to the diameter of the pore. The pores of the present hexagonal form of these materials are believed to be essentially cylindrical.

The equilibrium benzene adsorption capacity characteristic of this material is measured on the basis of no pore blockage by incidental contaminants. For instance, the sorption test will be conducted on the crystalline material phase having any pore blockage contaminants and water removed by ordinary methods. Water may be removed by dehydration techniques, e.g. thermal treatment. Pore blocking inorganic amorphous materials, e.g. silica, and organics may be removed by contact with acid or base or other chemical agents such that the detrital material will be removed without detrimental effect on the mesoporous crystal described herein.

The following description provides examples of how physisorption measurements, particularly argon physisorption measurements, may be taken. Examples 22(a) and 22(b) of the aforementioned U.S. Pat. No. 5,098,684, filed Dec. 10, 1990, provide demonstrations of these measurements as applied to particular samples.

To determine the pore diameters of products with pores up to about 60 Angstroms in diameter, 0.2 gram samples of the products may be placed in glass sample tubes and attached to a physisorption apparatus as described in U.S. Pat. No. 4,762,010, which is incorporated herein by reference.

The samples may be heated to 300° C. for 3 hours in vacuo to remove adsorbed water. Thereafter, the samples may be cooled to 87° K. by immersion of the sample tubes in liquid argon. Metered amounts of gaseous argon may then be admitted to the samples in stepwise manner as described in U.S. Pat. No. 4,762,010, column 20. From the amount of argon admitted to the samples and the amount of argon left in the gas space above the samples, the amount of argon adsorbed can be calculated. For this calculation, the ideal gas law and the calibrated sample volumes may be used. (See also S. J. Gregg et al., *Adsorption, Surface Area and Porosity*, 2nd ed., Academic Press, (1982)). In each instance, a graph of the amount adsorbed versus the relative pressure above the sample, at equilibrium, constitutes the adsorption isotherm. It is common to use relative pressures which are obtained by forming the ratio of the equilibrium pressure and the vapor pressure $P_o$ of the adsorbate at the temperature where the isotherm is measured. Sufficiently small amounts of argon may be admitted in each step to generate, e.g., 168 data points in the relative pressure range from 0 to 0.6. At least about 100 points are required to define the isotherm with sufficient detail.

The step (inflection) in the isotherm indicates filling of a pore system. The size of the step indicates the amount adsorbed, whereas the position of the step in terms of $P/P_o$ reflects the size of the pores in which the adsorption takes place. Larger pores are filled at higher $P/P_o$. In order to better locate the position of the step in the isotherm, the derivative with respect to log $(P/P_o)$ is formed. The position of an adsorption peak in terms of log $(P/P_o)$ may be converted to the physical pore diameter in Angstroms by using the following formula:

$$\log(P/P_o) = \frac{K}{d-0.38}\left(\frac{S^4}{3(L-D/2)^3} - \frac{S^{10}}{9(L-D/2)^9} - \frac{S^4}{3(D/2)^3} + \frac{S^{10}}{9(D/2)^9}\right)$$

wherein d=pore diameter in nanometers, K=32.17, S=0.2446, L=d+0.19, and D=0.57.

This formula is derived from the method of Horvath and Kawazoe (G. Horvath et al., *J. Chem. Ena. Japan*, 16 (6) 470(1983)). The constants required for the implementation of this formula were determined from a measured isotherm of $ALPO_4$-5 and its known pore size. This method is particularly useful for porous materials having pores of up to about 60 Angstroms in diameter.

For materials having a pore size greater than 9 Angstroms, the plot of log $(P/P_o)$ vs. the derivative of uptake may reveal more than one peak. More particularly, a peak may be observed at $P/P_o$=0.0027. This peak reflects adsorption on the walls of the pores and is not otherwise indicative of the size of the pores of a given material.

A material with pore size of 39.6 Angstroms has a peak occurring at log $(P/P_o)$=-0.4 or $P/P_o$=0.4. A value of $P/P_o$ of 0.03 corresponds to 13 Angstroms pore size.

The above method of Horvath and Kawazoe for determining pore size from physisorption isotherms was intended to be applied to pore systems of up to 20 Angstroms diameter; but with some care as above detailed, its use can be extended to pores of up to 60 Angstroms diameter, as described above.

In the pore regime above 60 Angstroms diameter, however, the Kelvin equation can be applied. It is usually given as:

$$\ln(P/P_o) = \frac{-2V}{r_k RT} \cos\theta$$

where:
 =surface tension of sorbate
V=molar volume of sorbate
θ=contact angle (usually taken for practical reasons to be 0)
R=gas constant
T=absolute temperature
$r_k$=capillary condensate (pore) radius
$P/P_o$=relative pressure (taken from the physisorption isotherm)

The Kelvin equation treats adsorption in pore systems as a capillary condensation phenomenon and relates the pressure at which adsorption takes place to the pore diameter through the surface tension and contact angle of the adsorbate (in this case, argon). The principles upon which the Kelvin equation are based are valid for pores in the size range 50 to 1000 Angstroms diameter. Below this range the equation no longer reflects physical reality, since true capillary condensation cannot occur in smaller pores; above this range the logarithmic nature of the equation precludes obtaining sufficient accuracy for pore size determination.

The particular implementation of the Kelvin equation often chosen for measurement of pore size is that reported by Dollimore and Heal (D. Dollimore and G. R. Heal, *J. Applied Chem*, 14, 108 (1964)). This method corrects for the effects of the surface layer of adsorbate on the pore wall, of which the Kelvin equation proper does not take account, and thus provides a more accurate measurement of pore diameter. While the method of Dollimore and Heal was derived for use on desorption isotherms, it can be applied equally well to adsorption isotherms by simply inverting the data set.

Non-lamellar forms of materials described herein, such as MCM-48 and, especially, MCM-41, may be distinguished from other oxide materials in terms of their pore sizes and the uniformity of their pore systems. A distinctive feature of certain forms of MCM-41 and MCM-48 is that these materials are (1) non-lamellar (e.g., non-layered or non-pillared), (2) have pore sizes over 13 Angstroms (e.g., over 15 Angstroms, even over 20 Angstroms), and (3) have an X-ray diffraction pattern with at least one peak, e.g., at a d-spacing of at least about 18 Angstroms.

Another indication of the uniformity of pore systems in these materials is apparent from the physisorption characteristics of these materials. More particularly, the plots of log $(P/P_o)$ vs. the derivative of uptake may reveal sharp peaks not observed for other large-pore materials, such as amorphous materials and pillared, layered materials.

Another distinctive feature of materials described herein, especially MCM-41 and MCM-48, is the extremely large surface areas of these materials. More particularly, certain forms of MCM-41 and MCM-48 may have surface areas over 800 $m^2/g$. Especially distinct forms of these materials with high surface areas include those with especially large pore sizes (e.g., greater than 20 Angstroms or 30 Angstroms), particularly those materials which are observed to have uniform pore size distributions.

A further distinctive feature of materials described herein, especially MCM-41 and MCM-48, is the large pore volumes of these materials. One indication of the pore volumes of these materials is their benzene sorption capacity. Pore volumes may also be measured by physisorption measurements. Such measurements of certain forms of materials described herein, such as forms of MCM-41 and MCM-48 may reveal pore volumes of greater than 0.40 cc/g.

As mentioned hereinabove the large pore sizes of materials described herein may be confirmed by physisorption measurements, especially argon physisorption measurements. Another indication of large pore sizes of materials described herein may be provided by determining their ability to sorb large probe molecules, such as molecules having kinetic diameters of at least 8.5 Angstroms, e.g., 1,3,5-triisopropylbenzene.

X-ray diffraction data were collected on a Scintag PAD X automated diffraction system employing theta-theta geometry, Cu K-alpha radiation, and an energy dispersive X-ray detector. Use of the energy dispersive X-ray detector eliminated the need for incident or diffracted beam monochromators. Both the incident and diffracted X-ray beams were collimated by double slit incident and diffracted collimation systems. The slit sizes used, starting from the X-ray tube source, were 0.5, 1.0, 0.3 and 0.2 mm, respectively. Different slit systems may produce differing intensities for the peaks. The mesoporous materials described herein that have the largest pore sizes may require more highly collimated incident X-ray beams in order to resolve the low angle peak from the transmitted incident X-ray beam.

The diffraction data were recorded by step-scanning at 0.04 or less degrees of two-theta, where theta is the Bragg angle, and a counting time of 10 seconds for each step. The interplanar spacings, d's, were calculated in Angstrom units (A), and the relative intensities of the lines, $I/I_o$, where $I_o$ is one-hundredth of the intensity of the strongest line, above background, were derived with the use of a profile fitting routine. The intensities were uncorrected for Lorentz and polarization effects. The relative intensities are given in terms of the symbols vs=very strong (75–100), s=strong (50–74), m=medium (25–49) and w=weak (0–24). It should be understood that diffraction data listed as single lines may consist of multiple overlapping lines which under certain conditions, such as very high experimental resolution or crystallographic changes, may appear as resolved or partially resolved lines. Typically, crystallographic changes can include minor changes in unit cell parameters and/or a change in crystal symmetry, without a substantial change in structure. These minor effects, including changes in relative intensities, can also occur as a result of differences in cation content, framework composition, nature and degree of pore filling, thermal and/or hydrothermal history, and peak width/shape variations due to particle size/shape effects, structural disorder or other factors known to those skilled in the art of X-ray diffraction.

The equilibrium benzene adsorption capacity may be determined by contacting the crystalline material described herein, after dehydration or calcination at, for example, about 540° C. for at least about one hour and other treatment, if necessary, in an attempt to remove any pore blocking contaminants, at 25° C. and 50 torr benzene until equilibrium is reached. The weight of benzene sorbed is then determined as more particularly described hereinafter.

When used as a catalyst component, the crystalline material described herein should be subjected to treatment to remove part or all of any organic constituent. The present composition can also be used as a catalyst component (e.g., a support) in intimate combination with a hydrogenating component such as a metal, particularly a transition metal, especially tungsten, vanadium, molybdenum, rhenium, nickel, cobalt, chromium, manganese, or a noble metal such as platinum or palladium or mixtures thereof where a hydrogenation-dehydrogenation function is to be performed. Such component can be in the composition by way of co-crystallization, exchanged into the composition to the extent a Group IIIB element, e.g. aluminum, is in the structure, impregnated therein or intimately physically admixed therewith. Such component can be impregnated in or on to it such as, for example, by, in the case of platinum, treating the material with a solution containing a platinum metal-containing ion. Thus, suitable platinum compounds for this purpose include chloroplatinic acid, platinous chloride and various compounds containing the platinum amine complex.

The above crystalline material, especially in its metal, hydrogen and ammonium forms can be beneficially converted to another form by thermal treatment (calcination). This thermal treatment is generally performed by heating one of these forms at a temperature of at least 400° C. for at least 1 minute and generally not longer than 20 hours, preferably from about 1 to about 10 hours. While subatmospheric pressure can be employed for the thermal treatment, atmospheric pressure is desired for reasons of convenience, such as in air, nitrogen, ammonia, etc. The thermal treatment can be performed at a temperature up to about 750° C. The thermally treated product is particularly useful in the catalysis of certain hydrocarbon conversion reactions.

The crystalline material described herein, when employed either as a support or a catalyst in an organic compound conversion process may be dehydrated, at least partially. This dehydration can be done by heating to a temperature in the range of 200° C. to 595° C. in an atmosphere such as air, nitrogen, etc. and at atmospheric, subatmospheric or superatmospheric pressures for between 30 minutes and 48 hours. Dehydration can also be performed at room temperature merely by placing the composition in a vacuum, but a longer time is required to obtain a sufficient amount of dehydration.

The reaction mixture for preparing crystalline materials described herein may comprise a source of one or more oxides, an amphiphilic compound and a solvent or solvent mixture. This amphiphilic compound is also referred to herein as the primary organic agent (R') and is more particularly described hereinafter. The solvent or solvent mixture may comprise, for example, $C_1$–$C_6$ alcohols, $C_1$–$C_6$ diols and/or water, especially water. Optional components of the reaction mixture include (1) a source of alkali or alkaline earth metal (M), e.g. sodium or potassium, cations, (2) an additional organic agent (R"), hereinafter more particular described, and (3) an organic swelling agent, also referred to herein as an auxiliary organic agent (R'''), hereinafter more particularly described.

The reaction mixture may have the mole ratio

Solvent/(R'$_2$O+M$_2$O)

of at least 45. When R is cetyltrimethylammonium and this ratio is 10–45, the formation of the above-mentioned lamellar phase is favored. When R' is cetyltrimethylammonium and this ratio is 45–92, the formation of the above-mentioned cubic phase (MCM-48) is favored. When R' is cetyltrimethylammonium and this ratio is greater than 92, e.g., 92–300, the formation of the above-mentioned hexagonal phase (MCM-41) is favored. It will be understood that mixtures of these phases may be produced near the transition values of these ratios. For example, mixtures of the hexagonal phase and the cubic phase may be produced at ratios of 92–100.

The reaction mixture may have the mole ratio (R'$_2$O+R"$_2$O)/(SiO$_2$+Al$_2$O$_3$)

of 0.01–2.0, e.g., 0.03–1.0, e.g., 0.3–1.0, e.g., 0.3–0.6. This mole ratio is calculated on a basis wherein it is assumed that all of the hydrolyzable silicon and aluminum compounds in the reaction mixture are hydrolyzed. The pH of the reaction mixture may be from about 7 to 14, e.g., from about 9 to 14.

The components of the reaction mixture may be combined in any order. In some instances, it may be desired to combine the solvent and primary organic agent (R') prior to adding the source of oxide to this preformed mixture. Upon the formation of the reaction mixture, this mixture may, optionally, be subjected to an aging step at low temperature, e.g., from about 0° C. to about 50° C., for a short period of time, e.g., from about 30 minutes to about 2 hours. This aging step may take place in the presence of absence of agitation of the reaction mixture.

Crystallization of the reaction mixture may take place at elevated temperature, e.g., from about 50° C. to about 200° C., e.g., from about 95° C. to about 150° C., for about 4 to about 72 hours, e.g., from about 16 to about 60 hours. The crystallization may take place under reflux conditions. The crystallization may also take place in the presence of microwave radiation under conditions specified in U.S. Pat. No. 4,778,666.

Particular methods for making MCM-41 are described in the aforementioned U.S. Pat. No. 5,102,643.

In each of the above methods, batch crystallization of the present crystalline material can be carried out under either static or agitated, e.g. stirred, conditions in a suitable reactor vessel, such as for example, polypropylene jars or teflon lined or stainless steel autoclaves. Crystallization may also be conducted continuously in suitable equipment. The total useful range of temperatures for crystallization is noted above for each method for a time sufficient for crystallization to occur at the temperature used, e.g. from about 5 minutes to about 14 days. Thereafter, the crystals are separated from the liquid and recovered.

When TMA aluminosilicate is used as the source of silica and alumina in the reaction mixture, particularly high alumina forms of the present materials may be formed. It is believed that by supplying aluminosilicate already in solution increases the dispersion and incorporation of Al atoms in the M41S framework.

By adjusting conditions of the synthesis reaction for each method, like temperature, pH and time of reaction, etc., within the above limits, embodiments of the present material with a desired degree of crystallinity or a desired average pore size may be prepared. In particular, changing the pH, the temperature or the reaction time may promote formation of product crystals with different average pore size.

A primary organic agent (R') for use in preparing the present reaction mixture is an ammonium or phosphonium ion of the formula $R_1R_2R_3R_4Q^+$, i.e.:

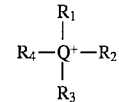

wherein Q is nitrogen or phosphorus and wherein at least one of $R_1$, $R_2$, $R_3$ and $R_4$ is aryl or alkyl of from 6 to about 36 carbon atoms, especially from 8 to 36 carbon atoms, e.g.—$C_{10}H_{21}$, —$C_{16}H_{33}$ and —$C_{18}H_{37}$, or combinations thereof, the remainder of $R_1$, $R_2$, $R_3$ and $R_4$ being selected from the group consisting of hydrogen, alkyl of from 1 to 5 carbon atoms and combinations thereof. The compound from which the above ammonium or phosphonium ion is derived may be, for example, the hydroxide, halide, silicate, or mixtures thereof.

An additional organic agent (R") may also be used. That additional organic agent may be the ammonium or phosphonium ion of the above primary organic agent formula wherein $R_1$, $R_2$, $R_3$ and $R_4$ together or separately are selected from the group consisting of hydrogen and alkyl of 1 to 5 carbon atoms and combinations thereof. Any such combination of organic agents may be in molar ratio of about 100/1 to about 0.01/1, first above listed organic agent/ additional organic agent (R'/R").

Non-limiting examples of R' capable of forming micelles include cetyltrimethylammonium, cetyltrimethylphosphonium, octadecyltrimethylphosphonium, cetylpyridinium, myristyltrimethylammonium, decyltrimethylammonium, dodecyltrimethylammonium and dimethyldidodecylammonium.

In addition to the above-mentioned primary organic agent (R') and the additional organic agent (R"), the reaction mixture may also contain an auxiliary organic agent (R'''). These auxiliary organic agents are compounds which are capable of swelling micelles. Such auxiliary organic agents may be selected from the group consisting of (1) aromatic hydrocarbons and amines having from 5 to 20 carbon atoms and halogen- and $C_1$–$C_{14}$ alkyl-substituted derivatives thereof, (2) cyclic aliphatic hydrocarbons and amines having from 5 to 20 carbon atoms and halogen- and $C_1$–$C_{14}$ alkyl-substituted derivatives thereof, (3) polycyclic aliphatic hydrocarbons and amines having from 6 to 20 carbon atoms and halogen- and $C_1$–$C_{14}$ alkyl-substituted derivatives thereof, (4) straight and branched aliphatic hydrocarbons and amines having from 3 to 16 carbon atoms and halogen-substituted derivatives thereof, and (5) combinations thereof.

In this group of auxiliary organic agents (R''') for use in the present method, the halogen substituent in substituted derivatives may be, for example, bromine. The $C_{1-14}$ alkyl substituent in the substituted derivatives may be linear or branched aliphatic chains, such as, for example, methyl, ethyl, propyl, isopropyl, butyl, pentyl and combinations thereof. Non-limiting examples of these auxiliary organic agents include, for example, p-xylene, trimethylbenzene, triethylbenzene and triisopropylbenzene. A particular example of such an auxiliary organic agent (R''') is 1,3,5-trimethylbenzene (i.e. mesitylene).

The mole ratio of the auxiliary organic agent to the primary organic agent (R'''/R') may be from about 0.02 to about 100, e.g., from about 0.05 to about 35.

Consistent with the ability of the auxiliary organic agent to swell micelies, the pore sizes of oxides prepared from reaction mixtures containing both auxiliary and primary organic agents have been observed to be substantially larger than the pore sizes of oxides prepared from reaction mixtures lacking auxiliary organic agents. When auxiliary organic agents are used in reaction mixtures, the pore sizes of oxide materials produced may be greater than 60 Angstroms.

The use of auxiliary organic agents in the preparation of MCM-41 is described in U.S. Pat. No. 5,057,296, the entire disclosure of which is expressly incorporated herein by reference.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

The oxides prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The present compositions are useful as catalyst components for catalyzing the conversion of organic compounds, e.g. oxygenates and hydrocarbons, by acid-catalyzed reactions. The size of the pores may be such that the spatiospecific selectivity with respect to transition state species is minimized in reactions such as cracking (Chen et al., "Shape Selective Catalysis in Industrial Applications", 36 *Chemical Industries,* pgs. 41–61 (1989) to which reference is made for a discussion of the factors affecting shape selectivity). Diffusional limitations are also minimized as a result of the very large pores in the present materials. For these reasons, the present compositions are especially useful for catalyzing reactions which occur in the presence of acidic sites on the surface of the catalyst and which involve reactants, products or transitional state species which have large molecular sizes, too great for undergoing similar reactions with conventional large pore size solid catalysts, for example, large pore size zeolites such as zeolite X, Y, L, ZSM-4, ZSM-18, and ZSM-20.

Thus, the present catalytic compositions will catalyze reactions such as cracking, and hydrocracking, and other conversion reactions using hydrocarbon feeds of varying molecular sizes, but with particular applicability to feeds with large molecular sizes such as highly aromatic hydrocarbons with substituted or unsubstituted polycyclic aromatic components, bulky naphthenic compounds or highly substituted compounds with bulky steric configurations, e.g. molecular sizes of about 13 Angstroms or more. The present catalytic compositions are particularly useful for reactions in which the molecular weight of the feed is reduced to a lower value, i.e. to reactions involving cracking such as cracking or hydrocracking. Cracking may be conducted at a temperature of from about 200° C. to about 800° C., a pressure of from about atmospheric to about 100 psig and contact time of from about 0.1 second to about 60 minutes. Hydrocracking may be conducted at a temperature of from about 150° C. to about 550° C., a pressure of from about 100 psig to about 3000 psig, and a weight hourly space velocity of from about 0.1 $hr^{-1}$ to about 100 $hr^{-1}$ with a hydrogen/hydrocarbon molar ratio of from about 0.1 to about 100.

The present catalytic compositions are especially useful for reactions using high molecular weight, high boiling or non-distillable feeds, especially residual feeds, i.e. feeds which are essentially non-distillable or feeds which have an initial boiling point (5% point) above about 1050° F. Residual feeds which may be used with the present catalytic compositions include feeds with API gravities below about 20, usually below 15 and typically from 5 to 10 with Conradsen Carbon Contents (CCR) of at least 1% by weight and more usually at least 5% or more, e.g. 5–10%. In some resid fractions the CCR may be as high as about 20 weight percent or even higher. The aromatic contents of these feeds will be correspondingly high, as may the contents of heteroatoms such as sulfur and nitrogen, as well as metals. Aromatics content of these feeds will usually be at least 50 weight percent and typically much higher, usually at least 70 or 80 weight percent, with the balance being principally naphthenes and heterocyclics. Typical petroleum refinery feeds of this type include atmospheric and vacuum tower resids, asphalts, aromatic extracts from solvent extraction processes, e.g. phenol or furfural extraction, deasphalted oils, slop oils and residual fractions from various processes such as lube production, coking and the like. High boiling fractions with which the present catalytic compositions may be used include gas oils, such as atmospheric gas oils; vacuum gas oils; cycle oils, especially heavy cycle oil; deasphalted oils; solvent extracts, such as bright stock; heavy gas oils, such as coker heavy gas oils; and the like. The present catalytic materials may also be utilized with feeds of non-petroleum origin, for example, synthetic oils produced by coal liquefaction, Fischer-Tropsch waxes and heavy fractions and other similar materials. Another example of a particular feed is shale oil.

As in the case of many catalysts, it may be desired to incorporate the new oxide composition with another material resistant to the temperatures and other conditions employed in organic conversion processes. Such materials include active and inactive materials and synthetic or naturally occurring zeolites as well as inorganic materials such as clays, silica and/or metal oxides such as alumina, titania and/or zirconia. The latter may be either naturally occurring or in the form of gelatinous precipitates or gels including mixtures of silica and metal oxides. Use of a material in conjunction with the new crystal, i.e. combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated with naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

It may be desirable to provide at least a part of the foregoing matrix materials in colloidal form so as to facilitate extrusion of the bound catalyst components(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The following examples illustrate the synthesis method of the present invention.

EXAMPLE 1

Forty five grams of 25% TMA hydroxide is added to 300 grams of TMA silicate solution obtained from SACHEM Chemicals (10% $SiO_2$ and TMA/Si=0.5). Following addition of 12 grams of aluminum isopropoxide, the mixture is placed in the steambox at a temperature of about 95° C. and autogenous pressure. After one hour, clear aluminosilicate solution having an Si/Al=17 is obtained. The amount of aluminum may be increased by a factor of 2 by addition of more aluminum isopropoxide and the solution remains clear.

EXAMPLE 2

Thirty four grams of aluminum isopropoxide is added to 200 grams of TMA silicate solution obtained from SACHEM Chemicals (10% $SiO_2$ and TMA/Si=5). Clear solution of TMA aluminosilicate is obtained after heating in the steambox at 95° C. for one hour or upon stirring for 20 hours at room temperature.

The synthesis method of the present invention provides a convenient route to the preparation of TMA aluminosilicate. TMA aluminosilicate is useful for producing MCM-41 with a high alumina content.

Changes and modifications in the specifically described embodiments can be carried out without departing from the scope of the invention which is intended to be limited only by the scope of the appended claims.

I claim:

1. A method for the synthesis of TMA aluminosilicate solution which comprises:

admixing a source of solid silica and tetramethylammonium hydroxide and heating the admixture at a temperature in the range of from about 40° C. to about 150° C. to produce a tetramethylammonium silicate solution intermediate product; and dissolving a hydrolyzable aluminum compound in said tetramethylammonium silicate intermediate product to produce tetramethylammonium aluminosilicate solution.

2. The method of claim 1, wherein said silica is in said admixture in an amount in the range of from about 1 wt. % to about 30 wt. %.

3. The method of claim 1, wherein said silica is amorphous silica.

4. The method of claim 1, wherein said tetramethylammonium hydroxide is in said admixture in an amount in the range of from about 1 wt. % to about 25 wt. %.

5. The method of claim 1, wherein said tetramethylammonium silicate intermediate product has a tetramethylammonium to silicon ratio in the range of from about 0.1 to about 2.

6. The method of claim 1, wherein said hydrolyzable aluminum compound is aluminum isopropoxide.

7. The method claim 1, wherein said hydrolyzable aluminum compound is sodium aluminate.

8. The method of claim 1 wherein said hydrolyzable aluminum compound is added in an amount corresponding to a silica to alumina ratio of at least 2.

9. The method of claim 1, wherein said tetramethylammonium aluminosilicate product has a silica to alumina ratio of at least 2.

10. The method of claim 1, wherein said heating is for a time in the range of about 1 minute to about 24 hours.

* * * * *